United States Patent [19]

Gossen et al.

[11] Patent Number: 5,602,300
[45] Date of Patent: Feb. 11, 1997

[54] PROCESS FOR DETECTING MUTATIONS, TRANSGENIC MAMMAL TRANSGENIC MAMMALIAN CELL, AND PROCESS FOR TESTING AGENTS OR CONDITIONING FOR MUTAGENIC PROPERTIES

[75] Inventors: Jan A. Gossen, Waddinxveen; Jan Vijg, Zegveld, both of Netherlands

[73] Assignee: Ingeny B.V., Netherlands

[21] Appl. No.: 122,562

[22] PCT Filed: Apr. 2, 1992

[86] PCT No.: PCT/NL92/00062

§ 371 Date: Dec. 29, 1993

§ 102(e) Date: Dec. 29, 1993

[87] PCT Pub. No.: WO92/17605

PCT Pub. Date: Oct. 15, 1992

[30] Foreign Application Priority Data

Apr. 2, 1991 [NL] Netherlands ............... 9100567

[51] Int. Cl.⁶ ............... C12N 5/00; C12N 15/00; A61K 49/00
[52] U.S. Cl. ............... 800/2; 800/DIG. 1; 424/9.2; 435/4; 435/6; 435/29; 435/172.3; 435/325; 435/352; 435/353; 435/354; 935/19; 935/59; 935/70; 935/77; 935/84
[58] Field of Search ............... 424/9; 435/4, 5, 435/6, 7.21, 7.37, 172.1, 172.3, 240.2, 29; 800/2, DIG. 1; 935/19, 59, 70, 79, 84, 77

[56] References Cited

U.S. PATENT DOCUMENTS 5,128,256 7/1992 Huse et al. ............... 435/172.3

5,347,075 9/1994 Sorge ............... 800/2

FOREIGN PATENT DOCUMENTS 0353812 2/1990 European Pat. Off. .

OTHER PUBLICATIONS

Gerhardt et al (1981) Manual of Methods for General Bacteriology pp. 229–234.
Reik (1993) In:Transgenic Animals, F Grosveld et al, eds, p. 103.
RM Strojek et al (1988) In Genetic Engineering: Principles and Methods v. 10, pp. 221–246.
M Dreyfus et al (1985) J Mol. Biol. 182:411–417.
J Lundeberg et al (1990) Genet Anal Techn Appl 7:47–52.
M Uhlen (1989) Nature 340:733–734.
"Germ–Line Transformation Of Mice," Ann. Rev. Genet., vol. 20, pp. 465–499 (1986).

*Primary Examiner*—Bruce R. Campell
*Attorney, Agent, or Firm*—Webb Ziesenheim Bruening Logsdon & Hanson, P.C.

[57] ABSTRACT

Detection of mutations in a lacZ gene including lacZ operator sequence functioning as marker gene located in a plasmid whereof one or more copies are introduced into the DNA of a mammal or of a mammalian cell, by isolating the DNA, cutting the plasmid out of the DNA, picking up the plasmid DNA with solid particles to which a lacZ operator binding material is bound, again releasing the plasmid from the solid particles after isolation and subsequently circularizing the plasmid, transforming a host restriction-negative, lacZ-negative and galE-negative bacterial host with the plasmid and separating transformants with mutated lacZ gene which grow on a lactose-containing medium from transformants with a non-mutated lacZ gene which do not grow on such a medium. A transgenic mammal model for mutation analysis.

26 Claims, 4 Drawing Sheets

5,602,300

PROCESS FOR DETECTING MUTATIONS, TRANSGENIC MAMMAL TRANSGENIC MAMMALIAN CELL, AND PROCESS FOR TESTING AGENTS OR CONDITIONING FOR MUTAGENIC PROPERTIES

BACKGROUND OF THE INVENTION

The invention relates to a process for detecting mutations in the DNA of a transgenic mammal or a transgenic mammalian cell, which DNA contains one or more copies of a marker gene located in a bacterial cloning vector, comprising isolating DNA from cells of the transgenic mammal or the transgenic mammalian cells, recovering the vector from the isolated DNA, transforming a suitable bacterial host with the recovered vector and determining mutations that have occurred in the marker gene on the basis of expression of the marker gene in the host.

The invention relates more particularly to a transgenic animal model provided with a marker gene which is integrated in the genome and which, after isolation of chromosomal DNA, can be recovered efficiently. After transfer of the marker gene to a bacteria incapable of host restriction, a selection is made on the presence of a mutated marker gene to determine the mutation frequency.

Such an animal model is of importance inter alia for testing agents for carcinogenic properties. All newly obtained compounds are in principle suspected of carcinogenicity. According to present day insights they could change the structure of heritable material present in every cell core. Such changes of the heritable material (mutations) can result among other things in cancer. Mutagenic agents (agents which cause mutations in the DNA) are as far as is known also carcinogenic and can likewise cause mutations in the germ cells, which can lead to hereditary genetic deviations. The mutagenicity of an agent is considered the most important criterion in determining the risk of developing cancer or hereditary deviations. It is therefore of particular importance to be able to determine the mutagenicity of an agent at an early stage.

The best known process to date for testing potentially mutagenic agents is the Ames test (Ames, 1973) wherein mutations are detected in bacteria. Although this test can be performed quickly because of the short generation times of a bacteria, extensive research has demonstrated that the predictive value of the Ames test is not 100% (Hay, 1988; Ashby and Tennant, 1988). Preference is therefore generally given to a combination of tests including tests with cultured (in vitro) mammalian cells.

There are at this moment only a few possibilities of detecting mutations in vivo in cells of higher animals. An example is the HPRT test, wherein mutations in the hypoxanthine phosphoribosyl transferase (HPRT) gene are detected on the basis of the 6-thioguanine resistance of the mutated cells (Albertini, 1982). This process is however labour-intensive and only allows measurements on cells that can still divide and are simple to culture. In addition, the artificial nature of the in vitro situation is a drawback to this process, whereby it is difficult to draw conclusions concerning induced mutations in organs and tissues and possible differences between them. An alternative hereto is the use of laboratory animals (particularly rodents) in long-term studies. Animals are exposed herein to a suspect agent and there is a wait to see whether or not tumours appear. This is a time-consuming process however which can last several years and requires many animals, particularly when low concentrations of a suspect agent are being tested. This makes the test very expensive, whereby agents which are positive in the Ames test are often not tested further and do not therefore become commercially available.

A good alternative is the use of transgenic animals as described by Vijg and Uitterlinden (1987), Lohman èt al. (1987) and Gossen et al. (1989) and in the European patent application EP-A-0 353 812. The transgenic mouse model described therein contains in each body cell, including the germ cells, a bacteriophage lambda vector in which the bacterial lacZ gene is cloned which serves as the mutation target gene. The vector can be recovered in efficient manner from chromosomal DNA by means of in vitro packaging of the vector in "empty" phage particles. The vector-containing phages are subsequently plated with $E.\ coli$ C host cells (which are host restriction-negative) wherein the selection takes place between mutated lacZ vectors (colourless) and non-mutated lacZ vectors (blue). The ratio between the number of colourless plaques and the number of blue plaques then indicates the mutation frequency. Rescue of marker genes from total chromosomal mammalian DNA in this efficient manner was first described by Gossen and Vijg (1988; see also the European patent application EP-A-0 353 812).

Using this process, mutation induction can in principle be studied in any tissue or organ of the above described transgenic animals. A drawback to this process however is that recovery of the bacteriophage lambda vectors by means of in vitro packaging is relatively expensive and labour-intensive. This is inherent to the nature of the vector which must be recovered and the principle forming the basis of determining the mutation frequency, namely the ratio between the number of mutated colourless plaques and the number of non-mutated blue plaques. With respect to the nature of the bacteriophage lambda vector which must be recovered, experiments have indicated that there exists a great degree of variability between different batches of packaging extracts; this means that prior to use of each separate batch the efficiency must first be determined. With respect to determining the mutation frequency on the basis of the ratio between the number of colourless mutated plaques and the number of blue non-mutated plaques, it can be stated that a reverse system wherein mutant vectors are coloured and non-mutant vectors are colourless is to be recommended. The spontaneous mutation frequency in different tissues and organs is in any case in the order of 1:100,000. In order to obtain reliable mutation frequencies in different tissues and organs at least 1 to 1.5 million plaques per organ or tissue have to be analyzed with the present system. The analysis of these numbers of plaques is exceptionally labour-intensive and requires large quantities of the packaging extract, the substrate X-gal and the petri dishes necessary for the analysis.

The invention now provides a process and an animal model which obviate these drawbacks.

SUMMARY OF THE INVENTION

The present invention provides in the first place a process for detecting mutations in the DNA of a transgenic mammal or transgenic mammalian cell, which DNA contains one or more copies of a linearized plasmid containing a lacZ gene including lacZ operator sequence as marker gene, comprising isolating DNA from cells of the transgenic mammal or the transgenic mammalian cells, fragmenting the isolated DNA by treatment with a restriction enzyme which can cut the plasmid out of the DNA, placing the fragmented DNA into contact with solid particles to which a lacZ operator binding material is bound, separating from non-bound DNA the solid particles having plasmid DNA bound thereon via the interaction between the lacZ operator binding material and the lacZ operator, releasing the plasmid DNA from the solid particles, circularizing the released plasmid DNA, transforming a host restriction-negative, lacZ-negative and galE-negative bacterial host with the obtained plasmid, and culturing transformed bacteria on a lactose-containing or lactose analogue-containing medium on which only the bacteria can grow which possess no β-galactosidase as a result of a mutation in the lacZ gene.

What is meant here by detecting of mutations is establishing whether and with what frequency mutations have occurred. The mutation frequency in the case of a transgenic laboratory animal can relate to the laboratory animal in its totality or to a determined collection of cells of the laboratory animal, such as cells of a particular organ or cells of a particular body part.

It is particularly recommended according to the invention that the plasmid is a plasmid suitable for transformation of *Escherichia coli* bacteria and a host restriction-negative, lacZ-negative and galE-negative *Escherichia coli* strain is used as bacterial host. The invention is not however limited to the use of *E. coli* bacteria. Other types of bacteria can also be considered suitable as bacterial host, provided suitable vector plasmids and host restriction-negative strains are available.

In order to enable separation of transformed and non-transformed bacteria the plasmid must contain a selection marker gene. Many options are known to the person skilled in the art for this purpose. Antibiotic-resistant genes are usually used for this purpose which provide the transformed bacteria with resistance against particular antibiotics. It is recommended that the plasmid suitable for cloning in *Escherichia coli* bacteria contains an ampicillin-resistance gene as selection marker gene and an ampicillin-sensitive, host restriction-negative, lacZ-negative and galE-negative *Escherichia coli* strain is used as bacterial host.

Although the plasmid in a linearized form can be incorporated directly into the mammalian DNA, it is greatly preferred according to the invention that the plasmid is introduced into the mammalian DNA as component of a bacteriophage vector wherein it is incorporated through insertion after being linearized using a restriction enzyme. It is recommended that the plasmid is incorporated in a bacteriophage lambda vector by insertion. Such a construction makes it possible to directly compare the present invention with the "Mutamouse" currently in use, i.e. a transgenic mouse on the basis of the system described by the inventors in their European patent application EP-A-0 353 812. The latter system acts according to the principle of recovering integrated bacteriophage (lambda) vectors from chromosomal DNA using commercially available packaging extracts. Using the described preferred embodiment of the present invention mutations in the same lacZ gene can be determined both by plasmid rescue and by bacteriophage lambda rescue. Use can be made hereof for confirmation of the results obtained.

A concrete preferred embodiment of the invention is that it is the plasmid pUR288 that is cloned in the unique EcoRI site of the bacteriophage lambda vector gt10 and this restriction enzyme EcoRI is used for fragmenting the isolated DNA.

The mammalian DNA can be both DNA of mammalian cells cultured in vitro and DNA of a transgenic mammal. In the latter case this will usually involve (small) rodents such as rats and mice. It is preferred that the plasmid is introduced into the DNA of a transgenic mouse or rat.

In a particularly preferred embodiment magnetic particles are used as solid particles. Through use of magnetic particles a separation can be brought about in very simple and efficient manner between the DNA adhered to the particles and the non-bound DNA. The magnetic particles can be picked up out of the mixture in simple manner by using a magnet. Non-magnetic particles can however also be used. In that case a separation out of the mixture can be effected by filtering and/or centrifuging and washing.

To enable selective picking up of the plasmid DNA the solid particles are coated with a lacZ operator binding material. Referred to here as "material" is substantially proteinaceous or protein material. Such a lacZ operator binding material could for instance be an antibody (polyclonal or monoclonal) with specific affinity for the lacZ operator. In a concrete preferred embodiment the lacZ operator binding material consists of protein material comprising a LacI repressor, i.e. LacI repressor protein or LacI repressor fusion protein. This material can be bound directly to the solid particles but is preferably bound indirectly to the solid particles. It is preferred that for isolating plasmid DNA, solid particles are used to which anti-β-galactosidase and LacI-repressor/β-galactosidase fusion protein are successively bound.

After the solid particles with plasmid DNA bound thereto have been separated from non-bound DNA, the plasmid DNA bound to the particles must be released again from the particles. In the case that for instance a protein material comprising LacI repressor as lacZ operator binding material is bound to the solid particles, use can be made for this purpose of agents having a greater affinity for the LacI repressor or the lacZ operator than the LacI repressor and the lacZ operator have for one another. It is recommended that for the release of plasmid DNA from the solid particles isopropyl β-D-thiogalactoside (IPTG) is used, which eliminates the bonding between the LacI repressor and the lacZ operator.

The invention relates further to a transgenic mammal, comprising in the mammalian DNA one or more copies of a plasmid containing a lacZ gene including lacZ operator sequence. The plasmid is preferably a plasmid suitable for cloning in *Escherichia coli* bacteria which preferably contains an ampicillin-resistance gene as selection marker gene and is preferably introduced into the mammalian DNA as component of a bacteriophage vector, preferably a bacteriophage lambda vector, wherein it is incorporated through insertion after being linearized using a restriction enzyme. A concrete embodiment according to the invention is a transgenic mammal in which it is the plasmid pUR288 that is cloned in the unique EcoRI site of the bacteriophage lambda Vector gt10. The transgenic mammal is preferably a transgenic rodent, preferably a transgenic mouse or rat.

The invention further relates to a transgenic mammalian cell which comprises in the mammalian DNA one or more copies of a plasmid containing a lacZ gene including lacZ operator sequence. The plasmid is preferably a plasmid suitable for cloning in *Escherichia coli* bacteria. This plasmid preferably contains an ampicillin-resistance gene as selection marker gene. The plasmid is preferably introduced into the mammalian DNA as component of a bacteriophage vector, preferably a bacteriophage lambda vector, wherein it is incorporated through insertion after being linearized using a restriction enzyme. In a concrete transgenic mammalian cell it is plasmid pUR288 that is cloned in the unique EcoRI site of the bacteriophage lambda vector gt10. In preference the transgenic mammalian cell is a transgenic rodent cell, preferably a transgenic mouse or rat cell.

The invention provides an in vivo process for testing agents or conditions for mutagenic properties by exposing one or more transgenic mammals according to the invention to an agent or condition for testing and in the above described manner subsequently detecting mutations in the lacZ gene functioning as marker gene. It is also possible herein to work in cell- or organ-specific manner to determine differences in mutagenicity of the tested agent or condition for different cells or organs.

The invention also provides an in vitro process for testing agents or conditions for mutagenic properties by exposing transgenic mammalian cells according to the invention to an agent or condition for testing and in the above described manner subsequently detecting mutations in the lacZ gene functioning as marker gene.

DETAILED DESCRIPTION OF THE INVENTION

The invention will be further elucidated hereinbelow with reference to a concrete preferred embodiment which relates to a new transgenic mouse.

The invention, which relates for instance to a transgenic mouse wherein the marker gene is situated in a plasmid inside a bacteriophage lambda vector which is integrated in a number of copies on one of the chromosomes, does not have the above stated limitations of the known processes for determining mutations in DNA. In the animal model according to the invention the recovery of the marker gene is particularly efficient because it makes use of a plasmid as bacterial cloning vector and lacZ gene including lacZ operator sequence as marker gene, whereby the strong and specific bonding of LacI repressor protein to the operator sequence which precedes the bacterial lacZ gene in the plasmid can be utilized to recover the vector. By further making use of magnetic beads having bound thereto an antibody directed against β-galactosidase that is subsequently coupled to the β-galactosidase-LacI repressor fusion protein (LacI/Z), the lacZ marker gene can, after bonding with the LacI repressor protein, easily be isolated from chromosomal DNA using a magnet. The binding between the operator sequence of the marker gene and the repressor protein can be eliminated by adding IPTG (isopropyl β-D-thiogalactoside). Due to the much greater affinity of IPTG for the LacI repressor the marker gene-containing plasmid DNA will be released in solution. The plasmids obtained are then circularized and transferred to a bacterial host which is only capable of growth (on a lactose-containing or lactose analogue-containing medium) when a mutated marker gene is incorporated. (E. coli, amp-negative, host restriction-negative, lacZ-negative, galE-negative). By relating the number of colonies to the number of isolated marker genes the spontaneous or induced mutation frequency in all tissues and organs of the transgenic mouse can thus be precisely and rapidly determined in simple manner. The expensive and time-consuming measurement of hundreds of thousands of plaques is hereby avoided.

The above described process for isolating marker gene molecules from total chromosomal DNA wherein use is made of the strong binding between the LacI repressor protein and the operator sequence has not been described previously in the literature. A similar process has been described for isolating DNA-binding proteins (Levens and Howly, 1985), which process is likewise based on the great affinity of the LacI repressor protein for the operator sequence. Use of the LacI repressor-operator binding for rapid purifying of the marker gene lacZ from chromosomal DNA for the purpose of mutation analysis has however, as already stated, not been proposed before. Preparatory use of magnetic bead technology and the known binding between the LacI repressor protein and the lacZ operator sequence in purifying of specific DNA sequences directly from chromosomal DNA encompasses a unique field of use, namely that of mutation analysis. Within this technological field direct selection is usual, while according to the invention as many copies of the marker gene as possible are first isolated.

An important aspect of the present invention is the efficiency with which plasmids integrated into the genome of higher organisms can be recovered. Earlier research by inter alia the present inventors (Gossen and Vijg, 1988; European patent application EP-A-0 353 812) to determine the recovery efficiency of bacteriophage lambda vectors from total chromosomal DNA of transgenic mice using different E. coli host strains demonstrated that only E. coli host strains could be used that are incapable of host restriction. E. coli strains incapable of host restriction are necessary because bacteriophage lambda vectors are modified after introduction into the genome of an animal. The modified DNA is recognized as such after introduction into a bacterial cell and immediately broken down by host restriction systems. The same is true for the recovery of plasmid vectors.

A mutation model based on integrated plasmids is not per se self-evident because it is known that the recovery of bacteriophage lambda vectors from genomic DNA is more efficient than recovery of plasmids. Plasmid rescue from genomic DNA is uneconomical due to the necessity of circularizing the lineared plasmid at very low concentration, that is, in high volumes. This has until now stood in the way of a successful application of a mutation model based on integrated plasmids.

The present invention does not have the above limitations due to the use of a rapid purifying step, namely efficient separation of the marker gene-containing plasmid from chromosomal DNA by binding LacI repressor protein coupled to magnetic beads to the operator sequence preceding the lacZ gene. Due to this purifying step essentially all the excess chromosomal DNA is removed and the circularizing can be efficiently performed thereafter in a small volume.

Using the above stated principle the present invention makes a transgenic animal model having in each body cell (including the germ cells) a marker gene that can easily be recovered and analyzed for the presence of mutations, eminently suited for testing agents suspected of mutagenicity. After binding with the LacI repressor complex the integrated plasmid can be recovered with great efficiency and transferred to an E. coli host cell (host restriction-negative) for determining the mutation frequency.

In order to be capable of being able to detect mutant lacZ genes simply it is desirable to utilize a selection system wherein the non-mutant colonies do not survive in favour of the mutant colonies. This is realized according to another aspect of the invention by making use of a galE-negative E. coli strain. If after purifying the lacZ-containing plasmids are transferred to an E. coli host that is host restriction-negative, lacZ-negative and galE-negative, only those cells which have incorporated a mutated plasmid will grow after plating on a lactose-containing or lactose analogue containing medium; E. coli cells which have incorporated a non-mutated plasmid will convert lactose or analogue to galactose as a result of the presence of the β-galactosidase. Further conversion of galactose is however not possible due to the mutation in the galE gene. This leads to an accumulation of the toxic by-product UDP-galactose, whereby the cell dies (Malamy, 1966). Use of galE-negative strains for mutation analysis in higher animals is new. This form of selection is also possible with bacteriophage lambda vectors.

The present invention therefore has two components, namely (1) technical components which ensure rapid purifying of integrated plasmids from total chromosomal mammalian DNA and a simple detection of mutated marker genes, and (2) biological components in the form of a new type of transgenic mammals and a particular type of bacterial host for detecting mutated marker genes, resulting in a transgenic animal model using which the above technical components can be used directly as a new in vivo mutation model.

The methodologies used according to the invention, including the magnetic bead technology for purifying marker genes from total chromosomal mammalian DNA and the use of a galE-, lacZ- and host restriction-negative E. coli strain for determining the mutation frequency in simple manner make the transgenic mouse model described herein eminently suitable for an in vivo mutation model. An important aspect of the transgenic mouse model according to the invention is the relatively low cost involved in the testing of potentially carcinogenic agents. By way of comparison, the costs of testing a possibly carcinogenic agent using long-term studies in rodents amounts to about 2 million guilders (Goldberg and Frazier, 1989) and, using the transgenic mouse model described in the European patent application EP-A-0 353 812 based on the recovery of bacteriophage lambda vectors, approximately 120,000 guilders. The latter costs are based on the analysis of 40 animals wherein the mutation frequency is determined in one organ and will therefore be a multiple hereof when more organs are tested. In contrast, the costs of using the transgenic mouse model described here will, when one organ is tested, amount to approximately 20,000 guilders. The considerable cost reduction is obtained mainly due to the combined use of the magnet bead technology and a galE-negative, lacZ-negative and host restriction-negative E. coli host and forms an important part in the use of a transgenic animal model for mutation analysis in vivo.

Experiment 1
Making transgenic mouse strain Ingeny M1.

The vector used was the bacteriophage lambda-gt10 vector (Promega B. V. of Leiden) in which the plasmid pUR288 is cloned in the unique EcoRI site (FIG. 1). The pUR288 plasmid contains a pBR322 Ori for replication, the ampicillin gene, the lacZ operator sequence and the whole lacZ gene (Ruther and Muller-Hill, 1986). The vector was transferred to the germ line of CD2 (Balb/c×DBA/2) mice by means of microinjection of fertilized egg-cells (Hogan et al., 1986). Balb/c and DBA/2 are two mouse strains originating from the rodent colony of the TNO Institute for Ageing and Vascular Research (TNO-IVVO) in Rijswijk.

It is known from the literature that after microinjection of linear DNA into a pronucleus of a fertilized ovum the injected DNA integrates in the genome in head-to-tail arrangement at a random place (Palmiter and Brinster, 1986). FIG. 2A shows a schematic view of a head-to-tail integration of the plasmid-containing bacteriophage lambda vectors in the genome of a mouse. The integration of the lambda vectors in this manner is essential for recovery from chromosomal DNA by means of in vitro packaging. During the integration process the two 12 base pair cohesive ends form one intact cos site which is recognized by the terminase enzyme in the in vitro packaging extract. The lambda DNA between two intact cos sites is packaged in an empty phage particle. This is described extensively in European patent application EP-A-0 353 812. FIG. 2B shows that the plasmid-containing lambda vectors are indeed integrated head-to-tail in the genome of a mouse of the strain Ingeny M1 (ING3). This was demonstrated by Southern analysis of liver DNA. The chromosomal DNA is cut with the restriction enzyme DraI which cuts the plasmid-containing vector into a number of fragments including one fragment of 1.2 kb. This fragment, which contains an intact cos site, is only present after head-to-tail integration of lambda vectors. The autoradiogram in FIG. 2B shows that the 1.2 kb fragment is indeed present in chromosomal DNA of a mouse strain Ingeny M1. It has been found from interbreeding experiments that the associated concatemer is inherited in Mendelian manner.

Experiment 2
Purifying integrated plasmids from chromosomal DNA of mouse ING3.

FIG. 3 shows the purifying and circularizing of the linear pUR288 plasmid from chromosomal DNA of an Ingeny M1 transgenic mouse (ING3). To purify the lacZ-containing plasmid from chromosomal DNA the latter was cut beforehand with the restriction enzyme EcoRI (lane a). Circa $10^8$ magnetic beads (for instance Dyna-beads M-450 sheep-anti-mouse IgG, ITK Diagnostics B. V. of Uithoorn) were subsequently added to about 10 μg chromosomal DNA, to which beads were successively coupled an anti-β-galactosidase antibody (Promega B. V.) and a LacI-β-galactosidase fusion protein (Promega B. V.). The coupling of the anti-β-galactosidase antibody to the magnetic beads and the coupling of the LacI-β-galactosidase fusion protein to the anti-β-galactosidase antibody were performed according to standard protocols (of respectively ITK Diagnostics B. V. and Promega B. V.). After one hour at room temperature the magnetic beads with the lacZ-containing plasmid bound thereto were separated from the remaining chromosomal DNA using a magnet (ITK Diagnostics B. V.) and washed at least twice in 250 μl 50 mM Tris.HCl pH 8.0, 100 mM NaCl. The coupling between the LacI repressor protein and the operator sequence was terminated by adding the magnetic beads to 10 μl 50 mM Tris.HCl pH 8.0, 100 mM NaCl, 0.2% IPTG (lane b). Circularizing of the plasmid was performed according to standard protocols (Maniatis et al., 1982), 20 ng of purified plasmid were ligated using 0.02 U T4-ligase enzyme (Gibco BRL) in a total volume of 25 μl. Because in comparison with the linear plasmid the circularized plasmid has a lower migration velocity during agarose gel electrophoresis, the circularizing of the recovered pUR288 plasmid can be analyzed in simple manner (lane c).

Experiment 3
Determining the recovery efficiency of integrated plasmids from chromosomal DNA of mouse ING3.

The recovery efficiency of the lacZ-containing plasmid is determined by transferring a small part of the circularized pUR288 plasmids to competent cells by means of transformation. The transformation can be carried out with ampicillin-sensitive E. coli strains which are host restriction- and lacZ-negative such as: E. coli C (Gossen and Vijg, 1988), E. coli Sure (Stratagene, Westburg B. V. of Leusden) or DH5αMCR (Life Technologies B. V. of Breda). The transformation was performed by means of electroporation as described by Dower et al., 1988. The pUR288-containing *E. coli* cells were subsequently plated on LB Agar medium (Gibco BRL) containing ampicillin (50 μg/ml). After incubation of the plates overnight at 37° C. the number of colonies (A) is a measure of the rescue efficiency. In this experiment approximately 50,000 plasmids were recovered from about 5 μg chromosomal DNA pre-cut with the restriction enzyme EcoRI. The remaining circularized plasmids can then be transferred to an *E. coli* host (amp-negative, lacZ-negative and host restriction-negative) which is sensitive to galactose (galE-negative). After transformation the *E. coli* cells were plated on MM/LB medium (4:1 vol/vol) containing phenylgalactoside (0.05%; Sigma), IPTG (20 μg/ml; Gibco BRL), and ampicillin (50 μg/ml; Merck). Only cells which as a result of a mutation in the lacZ gene have no β-galactosidase are not capable of converting phenylgalactoside can grow on this medium. The number of colonies (B), after incubation of the plates overnight at 37° C., is a measure for the number of mutants. The mutation frequency is subsequently determined by the ratio B/A.

Experiment 4

Recovery of integrated bacteriophage lambda vectors from chromosomal DNA of a transgenic animal.

For purposes of comparison lacZ recovery experiments were done with the Ingeny M1 mouse strain by means of bacteriophage lambda instead of plasmid rescue. Rescue of the plasmid-containing bacteriophage lambda vector was performed by adding a maximum of 10 μg chromosomal DNA to an in vitro packaging extract (Stratagene, Westburg B. V. of Leusden). After incubation of the extract at 22° C. for two hours the extract was diluted with 500 μl SM buffer (100 mM NaCl, 8 mM $MgSO_4.H_2O$, 50 mM Tris. Cl pH 7.5) and the recovery efficiency was determined by means of plating the approximately 5 μl phage solution with *E. coli* C (lacZ-negative and host restriction-negative) host cells (Maniatis et al., 1982). Circa 500,000 vectors could be recovered in this manner from about 10 μg liver DNA of a transgenic mouse of strain Ingeny M1 (ING3). The mutation frequency is defined as the ratio between the number of colourless (lacZ gene mutated) and blue (lacZ gene non-mutated) plaques.

REFERENCES

Figure 1:
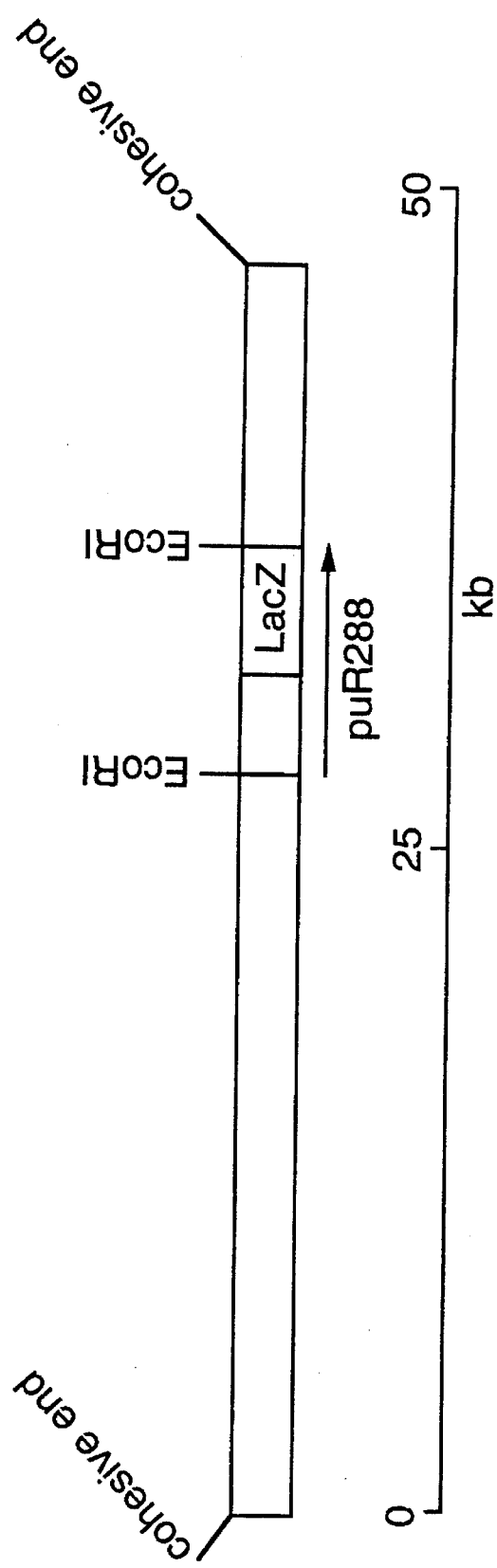
FIG. 1 is a schematic representation of the pUR288 plasmid-containing bacteriophage lambda vector gt-10 as described in experiment 1.
Figure 2A:
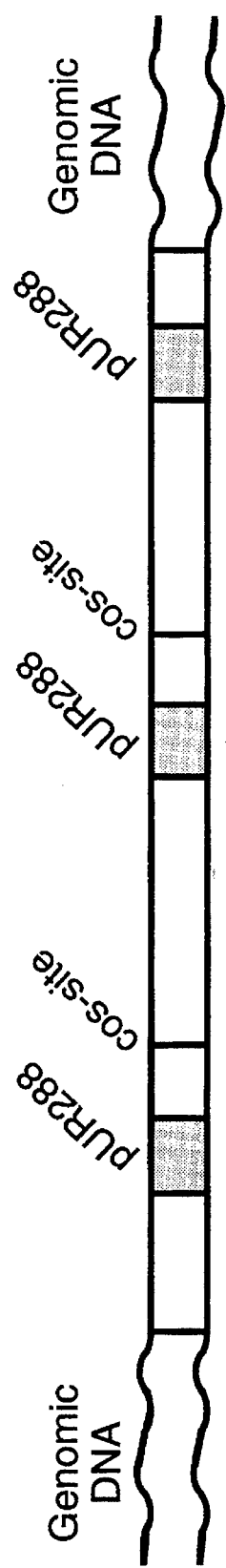
FIG. 2a is a schematic representation of a head-to-tail integration of the vector in the genome of a mouse.
Figure 2B:
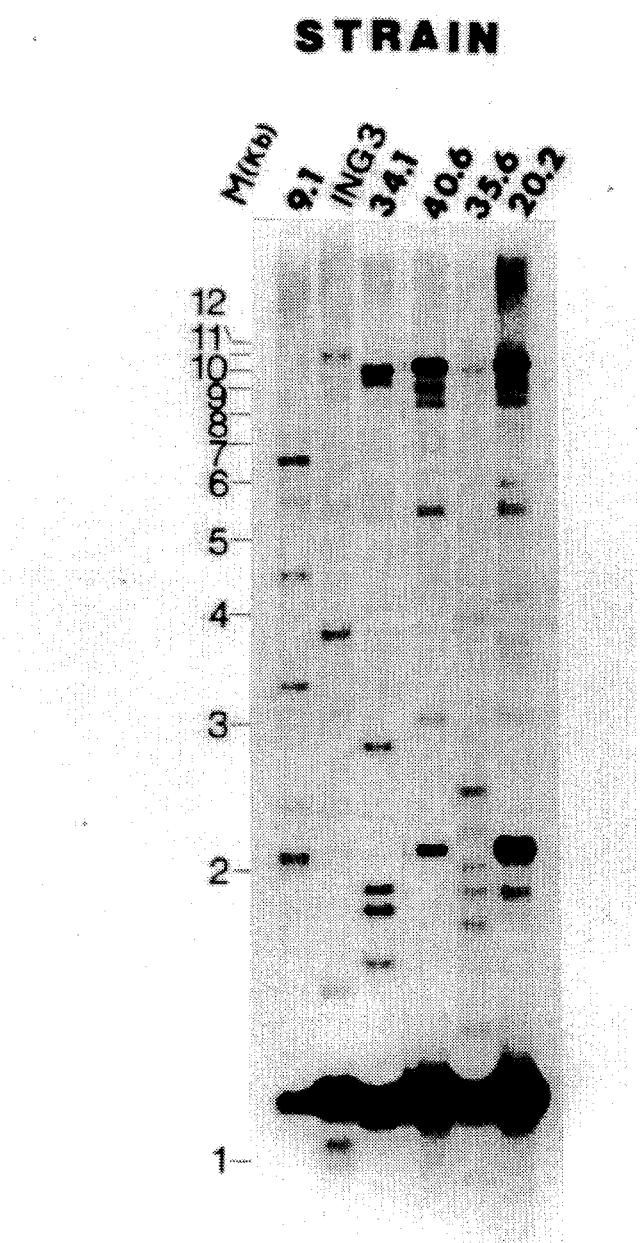
FIG. 2b is a representation of the autoradiogram obtained after Southern blotting of liver DNA of different transgenic mice cut with the restriction enzyme DraI.
Figure 3:
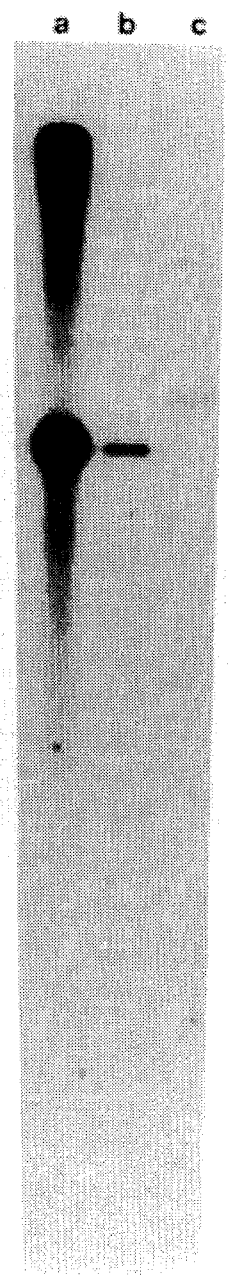
FIG. 3 shows recovery of the pUR288 plasmid from total chromosomal DNA of an Ingeny M1 transgenic mouse. The autoradiogram was obtained after Southern blotting of liver DNA of transgenic mouse ING-3 cut with the restriction enzyme EcoRI (lane a), the pUR288 plasmid purified using magnetic beads (lane b), the circularized pUR288 plasmid (lane c). The $^{32}$p-labelled pUR288 plasmid was used as probe.

Albertini, R. J. et al. Proc Natl. Acad. Sci. USA 79, 6617 (1982)

Ames, B. N., et al. Proc Natl. Acad. Sci. USA 70, 2281 (1973)

Ashby, J. and Tennant, R. W. Mutation Res. 204, 17–115 (1988)

Dower, W. J. et al. Nucleic Acids Res. 16, 6127–5145 (1988)

European patent application EP-A-0 353 812

Goldberg, A. M. and Frazier, J. M., Scientific American 261, 16–22 (1989)

Gossen, J. A. and Vijg, J. Nucleic Acids Res. 16, 9343 (1988)

Gossen, J. A., et al. Proc Natl. Acad. Sci. 86, 7971–7975 (1989)

Hay, A., Nature 332, 782–783 (1988)

Hogan, B. et al. Manipulating the Mouse Embryo: A Laboratory

Manual, Cold Spring Harbor Laboratory, Cold Spring Harbor, New York (1986)

Levens, D. and Howly, P. M. Mol. Cell. Boil. 5, 2307 (1985)

Lohman, P. H. M. et al. Mutation Res. 181, 227–234 (1987)

Malamy, M. H., Cold Spring Harbor Symposium on Quantitive Biology, Cold Spring Harbor Laboratory, Cold Spring Harbor, New York 31, 189–201 (1966)

Maniatis T. et al. Molecular Cloning: A Laboratory Manual, Cold Spring Harbor Laboratory, Cold Spring Harbor, New York (1982)

Palmiter, R. D. and Brinster, R. L. Annu. Rev. Genet. 20, 465 (1987)

Ruther, U. and Müller-Hill, B. EMBO 2, 1791–1793 (1983)

Vijg, J. and Uitterlinden, A. G. Mech. Ageing Dev. 41, 47–63 (1987)

We claim:

1. A process for detecting mutations in a lacZ gene integrated into the DNA of a transgenic mammal or transgenic mammalian cell, which DNA contains one or more copies of a linearized plasmid containing a lacZ gene including lacZ operator sequence as marker gene, comprising isolating DNA from cells of the transgenic mammal or the transgenic mammalian cells, fragmenting the isolated DNA by treatment with a restriction enzyme which can cut the plasmid out of the DNA, placing the fragmented DNA into contact with solid particles to which a lacZ operator binding material is bound, separating from non-bound DNA the solid particles having plasmid DNA bound thereon via the interaction between the lacZ operator binding material and the lacZ operator, releasing the plasmid DNA from the solid particles, circularizing the released plasmid DNA, transforming a host restriction-negative, lacZ-negative and galE-negative bacterial host with the obtained plasmid, and culturing transformed bacteria on a lactose-containing medium on which only the bacteria lacking galactosidase as a result of a mutation in the lacZ gene can grow.

2. A process as claimed in claim 1, wherein the plasmid is a plasmid suitable for cloning in *Escherichia coli* bacteria and said host restriction-negative, lacZ-negative and galE-negative bacterial host is *Escherichia coli*.

3. A process as claimed in claim 2, wherein the plasmid suitable for cloning in said *Escherichia coli* bacterial host contains an ampicillin-resistance gene as a selection marker gene and said bacterial host is ampicillin-sensitive.

4. A process as claimed in any of the claim 3, wherein the plasmid is introduced into the mammalian DNA as component of a bacteriophage vector wherein it is incorporated through insertion after being linearized using a restriction enzyme.

5. A process as claimed in claim 4, wherein said bacteriophage vector is a bacteriophage lambda vector.

6. A process as claimed in claim 5, wherein it is plasmid pUR288 that is cloned in the unique EcoRI site of the bacteriophage lambda vector gt10 and this restriction enzyme EcoRI is used for fragmenting the isolated DNA.

7. A process as claimed in any of the claim 1, wherein the plasmid is integrated into the DNA of a transgenic mouse or rat.

8. A process as claimed in any of the claim 1, wherein magnetic particles are used as solid particles.

9. A process as claimed in any of the claim 1, wherein protein material comprising a LacI repressor is used as lacZ operator binding material.

10. A process as claimed in claim 9, wherein for isolating plasmid. DNA use is made of solid particles to which anti-β-galactosidase and LacI-repressor/β-galactosidase fusion protein are successively bound.

11. A process as claimed in claim 10, wherein for the release of plasmid DNA from the solid particles isopropyl β-D-thiogalactoside (IPTG) is used, which eliminates the binding between the LacI repressor and the lacZ operator.

12. A transgenic mouse having incorporated into its DNA one or more copies of a plasmid containing a lacZ gene including lacZ operator sequence.

13. A transgenic mouse as claimed in claim 12, wherein the plasmid is a plasmid suitable for cloning in *Escherichia coli* bacteria.

14. A transgenic mouse as claimed in claim 13, wherein the plasmid suitable for cloning in *Escherichia coli* bacteria contains an ampicillin-resistance gene as selection marker gene.

15. A transgenic mouse as claimed in claim 12, wherein the plasmid is introduced into the mammalian DNA as component of a bacteriophage vector, wherein it is incorporated through insertion after being linearized using a restriction enzyme.

16. A transgenic mouse as claimed in claim 15, wherein the plasmid is incorporated in a bacteriophage lambda vector through insertion.

17. A transgenic mouse as claimed in claim 16, wherein it is plasmid pUR288 that is cloned in the unique EcoRI site of the bacteriophage lambda vector gt10.

18. A cultured mammalian cell having incorporated into its DNA one or more copies of a plasmid containing a lacZ gene including lacZ operator sequence.

19. A transgenic mammalian cell as claimed in claim 18, wherein the plasmid is a plasmid suitable for cloning in *Escherichia coli* bacteria.

20. A transgenic mammalian cell as claimed in claim 19, wherein the plasmid suitable for cloning in *Escherichia coli* bacteria contains an ampicillin-resistance gene as selection marker gene.

21. A transgenic mammalian cell as claimed in claim 20, wherein the plasmid is introduced into the mammalian DNA as component of a bacteriophage vector, wherein it is incorporated through insertion after being linearized using a restriction enzyme.

22. A transgenic mammalian cell as claimed in claim 21, wherein the plasmid is incorporated in a bacteriophage lambda vector through insertion.

23. A transgenic mammalian cell as claimed in claim 22, wherein it is plasmid pUR288 that is cloned in the unique EcoRI site of the bacteriophage lambda vector gt10.

24. A transgenic mammalian cell as claimed in claim 18 wherein said mammalian cell is a rodent cell.

25. A process for testing agents or conditions for mutagenic properties by exposing one or more transgenic mammals, having incorporated into the mammalian DNA one or more copies of a plasmid containing a lacZ gene including lacZ operator sequence, to an agent or condition for testing and subsequently detecting mutations in the lacZ gene functioning as marker gene by isolating DNA from cells of the transgenic mammal, fragmenting the isolated DNA by treatment with a restriction enzyme which can cut the plasmid out of the DNA, placing the fragmented DNA into contact with solid particles to which a lacZ operator binding material is bound, separating from non-bound DNA the solid particles having plasmid DNA bound thereon via the interaction between the lacZ operator binding material and the lacZ operator, releasing the plasmid DNA from the solid particles, circularizing the released plasmid DNA, transforming a host restriction-negative, lacZ-negative and galE-negative bacterial host with the obtained plasmid, and culturing transformed bacteria on a lactose-containing medium on which only bacteria lacking β-galactosidase as a result of a mutation in the lacZ gene can grow.

26. A process for testing agents or conditions for mutagenic properties by exposing cultured mammalian cells, having incorporated into the mammalian DNA one or more copies of a plasmid containing a lacZ gene including lacZ operator sequence, to an agent or condition for testing and subsequently detecting mutations in the lacZ gene functioning as marker gene by isolating DNA from the cultured mammalian cells, fragmenting the isolated DNA by treatment with a restriction enzyme which can cut the plasmid out of the DNA, placing the fragmented DNA into contact with solid particles to which a lacZ operator binding material is bound, separating from non-bound DNA the solid particles having plasmid DNA bound thereon via the interaction between the lacZ operator binding material and the lacZ operator, releasing the plasmid DNA from the solid particles, circularizing the released plasmid DNA, transforming a host restriction-negative, lacZ-negative and galE-negative bacterial host with the obtained plasmid, and culturing transformed bacteria on a lactose-containing medium on which only bacteria lacking β-galactosidase as a result of a mutation in the lacZ gene can grow.

* * * * *

UNITED STATES PATENT AND TRADEMARK OFFICE
CERTIFICATE OF CORRECTION

PATENT NO. : 5,602,300
DATED : February 11, 1997
INVENTOR(S) : Jan A. Gossen and Jan Vijg Page 1 of 3

It is certified that error appears in the above-indentified patent and that said Letters Patent is hereby corrected as shown below:

Title page, Item [54], and col. 1, line 2, after "MAMMAL" insert --,--

Title page, Item [54], and col. 1, line 4, "CONDITIONING" should read --CONDITIONS--.

Title page, Item '[56] References Cited, U.S. PATENT DOCUMENTS' insert --4,753,874  6/1988  Calos  435/6--.

Title page, Item '[56] References Cited, FOREIGN PATENT DOCUMENTS' insert 370,813  5/1990  EPO  C12Q  1/68;
8,901,173  10/1989  PCT  C12N  15/00--.

Title page, Item '[56] References Cited, OTHER PUBLICATIONS' insert --D. Levens and P. Howley, "Novel Method for Identifying Sequence-Specific DNA-Binding Proteins," Molecular and Cellular Biology, Sept. 1985, pp. 2307-2315;
J. Gossen and J. Vijg, "Transgenic Mice as a Model to Study Gene Mutations Application as a Short-Term Mutagenicity Assay," Mutation and the Environment, Part A, pp. 347-354--.

Column 4 Line 20 before "operator" delete --.--.

Column 7 Line 6 "gale gene" should read --galE gene--.

Column 9 Line 59 "$^{32}$p-labelled" should read --$^{32}$P-labelled.

Column 10 Lines 15-16 "Laboratory ¶ Manual" delete carriage return.

UNITED STATES PATENT AND TRADEMARK OFFICE
CERTIFICATE OF CORRECTION

PATENT NO. : 5,602,300  
DATED : February 11, 1997  
INVENTOR(S) : Jan A. Gossen and Jan Vijg Page 2 of 3

It is certified that error appears in the above-indentified patent and that said Letters Patent is hereby corrected as shown below:

```
Claim 1 Column 10 Line 55 delete "galactosidase" and
    insert --β-galactosidase--.

Claim 4 Column 10 Line 65 delete "any of the".

Claim 7 Column 11 Line 9 delete "any of the".

Claim 8 Column 11 Line 12 delete "any of the".

Claim 9 Column 11 Line 14 delete "any of the".

Claim 10 Column 11 Line 18 delete --.-- between "plasmid"
    and "DNA".

Claim 19 Column 11 Line 49 delete "Transgenic" and insert
    --A cultured--.

Claim 20 Column 11 Line 52 delete "Transgenic" and insert
    --A cultured--.

Claim 21 Column 11 Line 56 delete "Transgenic" and insert
    --A cultured--.

Claim 22 Column 12 Line 4 delete "Transgenic" and insert
    --A cultured--.

Claim 23 Column 12 Line 7 delete "Transgenic" and insert
    --A cultured--.
```

UNITED STATES PATENT AND TRADEMARK OFFICE
CERTIFICATE OF CORRECTION

PATENT NO. : 5,602,300
DATED : February 11, 1997
INVENTOR(S) : Jan A. Gossen and Jan Vijg It is certified that error appears in the above-indentified patent and that said Letters Patent is hereby corrected as shown below:

Claim 24 Column 12 Line 10 delete "Transgenic" and insert
--A cultured--.

Signed and Sealed this

Fifteenth Day of July, 1997

Attest:

BRUCE LEHMAN

*Attesting Officer*   *Commissioner of Patents and Trademarks*